United States Patent [19]

Cooper

[11] Patent Number: 5,641,744
[45] Date of Patent: Jun. 24, 1997

[54] TREATMENT OF DIABETES MELLITUS

[75] Inventor: Garth J. S. Cooper, Woodstock, England

[73] Assignee: Amylin Pharmaceuticals, Inc., San Diego, Calif.

[21] Appl. No.: 341,342

[22] Filed: Nov. 17, 1994

Related U.S. Application Data

[60] Continuation of Ser. No. 821,003, Jan. 15, 1992, abandoned, which is a division of Ser. No. 715,031, Jun. 10, 1991, Pat. No. 5,124,314, which is a continuation of Ser. No. 236,985, Aug. 26, 1988, abandoned.

[30] Foreign Application Priority Data

Aug. 26, 1987 [GB] United Kingdom ............ 8720115

[51] Int. Cl.⁶ .................... A61K 38/16; A61K 38/28
[52] U.S. Cl. ................... 514/4; 514/12; 530/303
[58] Field of Search ............... 514/4, 12; 530/303

[56] References Cited

U.S. PATENT DOCUMENTS

| | | | |
|---|---|---|---|
| 4,530,838 | 7/1985 | Evans | 514/11 |
| 4,687,839 | 8/1987 | Kempe | 530/324 |
| 4,697,002 | 9/1987 | Kempe | 530/324 |
| 4,720,483 | 1/1988 | Janz | 514/11 |
| 4,736,023 | 4/1988 | Evans | 536/23.51 |

FOREIGN PATENT DOCUMENTS

| | | |
|---|---|---|
| 156772 | 10/1985 | European Pat. Off. . |
| 188400 | 7/1986 | European Pat. Off. . |
| 263802 | 4/1988 | European Pat. Off. . |
| 270376 | 6/1988 | European Pat. Off. . |
| 2141430 | 12/1984 | United Kingdom . |
| 8501658 | 4/1985 | WIPO . |

OTHER PUBLICATIONS

Foord et al., Eur. J. Biochem. 170:373 (1987).
Sewell et al., Soc. Neurosci. Abs. 13:42 (1987).
Kimura et al., Neuropeptides 9:75 (1987).
Minvielle et al., FEBS Lett. 203:7 (1986).
Morris et al., Nature 308:746 (1984).
Craig et al., Biochem. Soc. Symp. 52:91 (1986).
Tippins et al., J. Hypertens., 4:5102 (1986).
Tippins et al., Biochem. Biophys. Res. Commun., 134:1306 (1981).
Holman et al., Peptides, 7:231 (1986).
Lenz et al., Gut, 26:550 (1985).
Westermark et al., Biochem. Biophys. Res. Commun. 140:827 (1986).
Westermark et al., Diabetologia, 30:887 (1987).
Westermark, et al., Proc. Nat. Acad. Sci. (USA), 84:3881 (1987).
Westermark et al., Am. J. Pathol., 127:414 (1987).
Cooper et al., Proc. Nat. Acad. Sci. (USA) 84:8628 (1987).
Cooper et al., Lancet 2:966 (1987).
Westermark et al., Am. J. of Pathology, vol. 127, No. 3, Jun. 1987, Islet Amyloid in Type 2 Human Diabetes Mellitus and Adult Diabetic Cats Contains a Novel Putative Polypeptide Hormone.

*Primary Examiner*—Christine M. Nucker
*Assistant Examiner*—Benet Prickril
*Attorney, Agent, or Firm*—Lyon & Lyon

[57] ABSTRACT

The present invention relates to methods of preparing a product or a composition containing amylin or amylin with insulin for treating diabetes mellitus.

17 Claims, 1 Drawing Sheet

TREATMENT OF DIABETES MELLITUS

This is a continuation of application Ser. No. 07/821,003 filed Jan. 15, 1992, now abandoned, which is a divisional of application Ser. No. 07/715,031 filed Jun. 10, 1991, now U.S. Pat. No. 5,124,314, which is a continuation of Ser. No. 07/236,985 filed Aug. 26, 1988, now abandoned.

Type 1 diabetes mellitus is a disease that affects large numbers of people, and results from the destruction of B-cells within the islets of Langerhans in the pancreas. The current therapy for type 1 diabetes is with parenteral administration of replacement doses of insulin. It is desirable that diabetic control be such that blood glucose levels be returned to near normal in order to avoid the long term complications of diabetes. Such therapy is, however, difficult to control in that it is frequently not easy to avoid the complication of hypoglycaemia, which may lead to morbidity, hypoglycaemic coma, and in infrequent cases to long term brain damage or death. It has long been known that, for reasons which are not fully understood, hypoglycaemia is a very frequent and very upsetting side-effect of insulin therapy.

Type 2 diabetes mellitus is about 8 to 10 times more prevalent than Type 1 diabetes, and may affect up to 4% of the adult population in Western countries. It is characterized by (1) a deficiency but not an absolute lack of insulin secretion which results in hyperglycaemia, and usually also by (2) varying degrees of resistance to the actions of insulin. In this form of diabetes, unlike Type 1, B-cells are retained in the islets in normal or only slightly reduced numbers. Islet amyloid is also found in most cases (Clark A., Cooper G. J. S. et al., Lancet Aug. 2, 1987).

British Patent Application 8709871 filed 27 Apr. 1987, describes a novel Peptide which is identical to or substantially homologous with the amino acid sequence.

```
            5    10   15   20   25   30   35
KCNTATCATQRLANFLVHSSNNFGAILSSTNVGSNTY
``` or an active subfragment thereof, Cooper et al., "Purification and Characterization of a Peptide from Amyloid-Rich Pancreases of Type 2 Diabetic Patients," *Proc. Natl. Acad. Sci. USA*, Vol. 84 (1987).

This may alternatively be written using the classical three letter designations of amino acid residues as follows:

```
1                    5                   10                  15
Lys Cys Asn Thr  Ala Thr Cys Ala  Thr Gln Arg Leu  Ala Asn Phe 16                   20                  25                  30
Leu Val His Ser  Ser Asn Asn Phe  Gly Ala Ile Leu  Ser Ser Thr 31                   35
Asn Val Gly Ser  Asn Thr Tyr
```

This novel peptide, provisionally named diabetes associated peptide or DAP and now renamed "amylin", has been isolated and characterized from the amyloid containing pancreases of type 2 diabetic humans. It is stated that amylin may be found to have clinical utility, such as appetite suppressant activity, and perhaps also vasodilator activity which could be either general activity or be specific for pancreas or islet blood flow.

A tumor-associated peptide similar in primary structure to amylin has been said to have been partially sequenced from a human insulinoma, and the N-terminal portion of a similar peptide incompletely sequenced from the pancreas of a diabetic cat (P. Westermark et al., Proc. Natl. Acad. Sci. USA, vol. 84, p 3881 to 3885, June 1987, Medical Sciences).

This peptide has been named insulinoma or islet amyloid polypeptide (IAPP), but there is said to be little doubt that the human and cat islet amyloid are of essentially similar chemical nature. Immunohistochemical techniques using a peroxidase technique suggest that IAPP is released locally from islet B-cells. Although the role of IAPP in the islet is stated to be unknown, its conservation and partial identity with CGRP were said to strongly indicate an important regulatory function.

Figure 1:
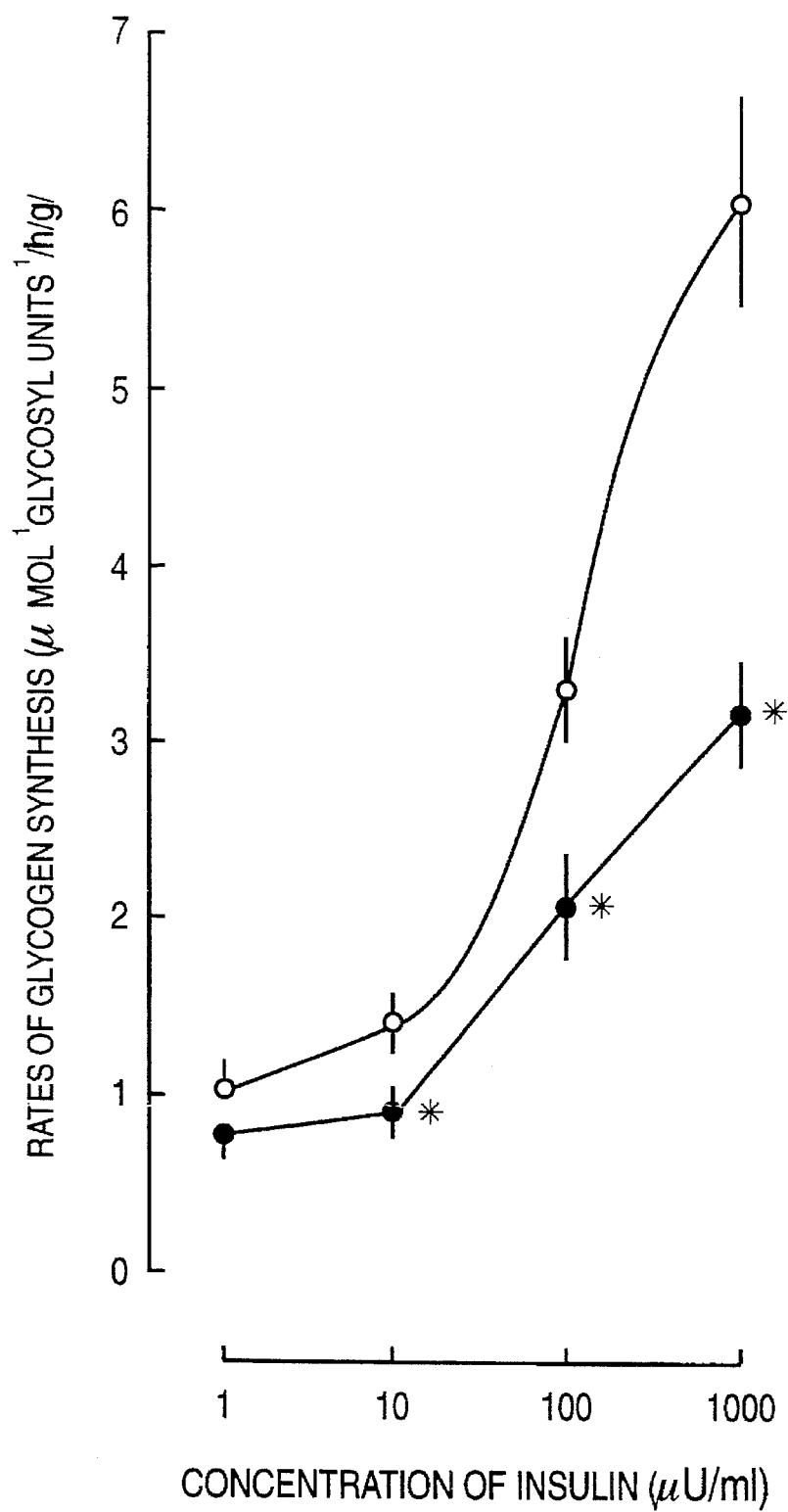
FIG. 1 shows the rate of glycogen synthesis against increasing insulin concentrations in the presence of amylin (closed circles) and in the absence of amylin (open circles).

Amylin is believed to contain thirty-seven amino acid residues and is structurally similar to calcitonin gene related peptide CGRP, having 46% identity with human CGRP-2. The following table compares the primary structures of 1) amylin with that of 2) human CGRP-2, 3) human CGRP-1 and 4) rat CGRP-1. Amino acid identity between peptides is indicated by underlining. Dotted areas indicate areas of displaced homology.

```
    1   5    10   15   20   25   30   35

1) KCNTATCATQRLANFLVHSSNNFGAILSSTNVGSNTY
                  ...

2) ACNTATCVTHRLAGLLSRSGGMVKSNFVPTNVGSKAF
                  ..

3) ACDTATCVTHRLAGLLSRSGGVVKNNFVPTNVGSKAF
                  ...

4) SCNTATCVTHRLAGLLSRSGGVVKDNFVPTNVGSEAF
                  ..
```

It is known that CGRP exerts significant effects on blood pressure and blood catecholamine levels when administered to rats.

In an article in the Lancet published on 2 Aug. 1987, A. Clark, G. J. S. Cooper et al. report that islet amyloid in twenty-two amyloid-containing type 2 diabetic subjects showed immunoreactivity with antisera to CGRP. This was inhibited by preabsorption of the antisera with amylin, which suggests that amylin is a major protein constituent of islet amyloid. Cooper et al., supra (1987), confirmed that amylin is a major component of islet amyloid. In addition CGRP/amylin immunoreactivity was found in islet cells of both diabetic and non-diabetic subjects, and preliminary studies show its presence in B-cells, Cooper et al. Lancet 1987, 2:964. This identification, together with the finding of a similar peptide in insulinomas, suggests that amylin may be co-secreted with insulin.

This invention arises from the idea that amylin or deamidated amylin or CGRP or a functional peptide fragment of amylin or deamidated amylin or CGRP, or a conservative variant of the amylin or deamidated amylin or CGRP or fragment, will be of use in the treatment of diabetes mellitus or hypoglycaemia. This idea was unexpected. Although it was known that both amylin and perhaps CGRP are associated in some way with diabetes mellitus, it had not previously been suggested that either might be useful in the treatment of the condition. The work on which this invention is based has been concerned with both amylin and CGRP. The invention extends to CGRP on the basis that this peptide has generally similar constitution and properties to amylin, and may therefore be expected to show the same surprising therapeutic effect.

Deamidated amylin may be in its carboxy terminated form (deamidated amylin) or alternatively in its carboxy terminally amidated form (amylin). The structure of the amidated form may be represented as:

where R is the residue of the peptide up to the peptide bond to the carboxy terminal residue, presently believed to be Tyrosine. Currently known forms of CGRP include a C-terminal amide group which is significant for their biological activity.

A functional peptide fragment of amylin or deamidated amylin or CGRP is meant to include a peptide fragment at least 5 amino acid residues in length, which performs in vivo a therapeutic function of the complete amylin or deamidated amylin or CGRP peptide. A conservative variant is meant a to include peptide which is substantially, though not completely, homologous with amylin or deamidated amylin or CGRP or the fragments thereof, but which is functionally equivalent thereto. (See M. O. Dayhoff, A Model of Evolutionary Change in Proteins, in "Atlas of Protein Sequence and Structure" Foundation, 1978, pages 345–352) See Cooper et al., P.N.A.S. (1987), supra.

According to a preferred aspect of the invention, a composition for use in the treatment of diabetes mellitus or hypoglycaemia comprises a) insulin and b) amylin or deamidated amylin or CGRP, or a functional peptide fragment of amylin or deamidated amylin or CGRP or fragment. The term insulin is here used to cover insulin of natural and synthetic origin and also functional peptide fragments of insulin and conservative variants of insulin or fragments thereof, such as may be used in the conventional treatment of diabetes mellitus.

Products according to the invention may conveniently be provided in the form of solutions suitable for parenteral administration. In many cases, it will be convenient to provide insulin and amylin or deamidated amylin or CGRP (or fragment or variant) in a single solution for administration together. In other cases, it may more advantageous to administer insulin, and amylin or deamidated amylin or CGRP (or fragment or variant), separately. A suitable administration regime may best be determined by a doctor for each patient individually. It will generally be preferably to formulate such that the molar ratio of insulin to amylin or deamidated amylin or CGRP (or fragment or variant) used for the treatment is from 100:1 to 0.1:1. A preliminary study has indicated that, like insulin immunoreactivity, amylin immunoreactivity and hence amylin, is absent from the islets of Langerhans in type 1 diabetics. It is therefore proposed that the type 1 diabetic syndrome results from a deficiency of not one (i.e. insulin as previously thought) but two (insulin and amylin or deamidated amylin or CGRP) hormones. As previously noted, the major problem with insulin treatment of diabetes is hypoglycaemia. It is likely that co-administration of insulin and amylin or deamidated amylin or CGRP may avoid this side effect. This may then allow:

Tighter diabetic control with reduced risk of hypoglycaemia. This applies to the treatment of type 1 diabetes mellitus, and also for type 2 diabetes mellitus (in the phase of secondary islet cell failure).

The use of amylin or deamidated amylin or CGRP for the therapy of recurrent hypoglycaemia complicating the insulin therapy of type 1 diabetes mellitus (or of type 2 diabetes mellitus).

The therapy of brittle diabetes (type 1 diabetes mellitus with increased risk of hypoglycaemia).

The therapy of the intractable hypoglycaemia which may complicate the course of the disease produced by insulin secreting tumours, such as insulinomas.

Although this invention is concerned with results and not with theories, the following explanation of the possible of mode of action of amylin (or CGRP) may be of interest.

1. Amylin or deamidated amylin is produced in the islets of Langerhans, almost certainly in the B-cell i.e. the same cell that produces insulin. Type 1 diabetes results from the destruction of B-cells in the islets of Langerhans. As these cells contain amylin or deamidated amylin, then it is very likely that type 1 diabetes is associated with a deficiency of amylin or amylin-NH$_2$ as well as insulin. Certainly, amylin or deamidated amylin is not seen in the islets of Langerhans in this condition.

2. Amylin and CGRP have been shown to modulate the rate of glucose induced insulin secretion from islet B cells in a number of model systems. (Ahren B, Martensson H, Nobin A. Effects of calcitonin gene-related peptide (CGRP) on islet hormone secretion in the pig. (Diabetologia 1987; 30:354–359.)

3. In isolated rat soleus muscles, amylin reduces the rate of glycogen synthesis in both the basal and the insulin-stimulated modes (see Example below).

When 2 and 3 are taken together, amylin (or CGRP) exerts a powerful modulating effect on insulin-induced storage of glucose as glycogen. As this may well be the mechanism whereby insulin resistance is caused in type 2 diabetes, then it may well be that hypersecretion of amylin or deamidated amylin (or CGRP) is a factor in the genesis of the insulin resistance found in that condition.

The actions if amylin (or CGRP), as seen above, modulate and reduce the hypoglycaemic effects of insulin, both by reducing the release of insulin in relation to a given glucose stimulus, and (more importantly in the case of type 1 diabetes) by reducing the rate of storage of glucose as glycogen. Hence, amylin (or CGRP) may induce "insulin resistance", and cushion the hypoglycaemic effects of insulin.

The efficacy of a preparation of amylin in the treatment of diabetes mellitus is dependent on the ability of the amylin to gain access to the circulation. To that end, preparations of amylin that are soluble are required. It has been demonstrated that certain processes may be used to solubilize amylin when present in amyloid masses, and these methods will also be of use in solubilizing amylin from other sources. Cooper, et al., Proc. Natl. Acad. Sci. USA, 84:8628–8623 (1987). They include (1) dissolution of amylin in guanidinium solutions, especially guanidinium hydrochloride, pH 7.5, buffered in 0.2M sodium monohydrogen phosphate/sodium dihydrogen phosphate; (2) dissolution of amylin in trifluoroacetic acid/acetonitrile solutions, especially 1.0% trifluoroacetic acid/67% acetonitrile; (3) dissolution of amylin in formic acid solution, especially 70% formic acid; and (4) the use of ultrasound to dissolve amylin. Experimental work also indicates that lyophilization may render amylin more soluble, perhaps by altering its physical state.

Comparison of the activity of amylin which has been chemically synthesized with that from natural sources indicates that the activity of amylin from these differing sources can be quantitatively different. It is possible that differences in activity can be caused by a lack during chemical synthesis to completely reconstitute the molecule into the natural conformation necessary for full biological activity. This is believed caused in part by failure to completely reconstitute the disulfide bond in the chemically synthesized material. It may also relate to the amidation of amylin to deamidated amylin. Therefore, it is useful to observe that the activity of amylin from different sources, i.e., extracted from the natural state, and chemically synthesized, may be different owing in part to amidation and to differing degrees of reconstitution of the natural secondary and tertiary structure of the molecule.

Reconstitution of the molecule in dilute aqueous solution at pH 8 produced a degree of biological activity. In view of the lower solubility of the synthetic material in solution in pH 8 water, however, improved reconstitution of synthetic amylin may be obtained by refolding material resulting from synthetic methods in an aqueous denaturing solution, for example, guanidinium or urea solutions, especially 6.0M guanidinium chloride or 8.0M urea, at a specified pH, especially a mildly alkaline pH between about 7.5 and about 9.0. Alternatively, solution for subsequent reconstitution may be effective in a non-aqueous, denaturing solvent, such as dimethyl formamide. Under such conditions, the reconstitution of the disulfide bond by mild oxidation, such as produced by solutions of potassium, ferricyanide or by exposure to atmospheric oxygen, are expected to produce optimal reconstitution of the disulfide bond.

For therapeutic use, it will be useful to have amylin preparations of differing durations of action, such as those in use for insulin. See Larner, J., "Insulin and Oral Hypoglycemic Drugs; Glucagon." (In Gilman, et al., Eds., The Pharmacologic Basis of Therapeutics, 7th Edition, MacMillan 1985, p. 1501–02). To that end, methods similar to those used for insulin are to be employed for therapeutic preparations of amylin. All such preparations may be used either alone, or in combination with appropriate combinations of insulin, for the treatment of diabetes mellitus, hypoglycemia and other conditions. These procedures and preparations include (1) reaction of amylin with zinc and protamine, according to the method of Hagedorn, et al., "Protamine Insulinate," JAMA 106:177–180 (1936), to produce an amylin preparation, the onset and duration of action of which is delayed compared with that of non-complexed amylin; (2) a suspension of the protamine-amylin prepared as above in a suitable aqueous buffer for parenteral administration; (3) crystalline amylin prepared by the crystallization of amylin in the presence of a zinc salt, especially zinc chloride, in a suitable buffer medium, and especially one of neutral pH (Larner, supra); (4) a suspension of crystalline zinc amylin in a suitable aqueous buffer, prepared as above, and suitable for parenteral administration; (5) a modified protamine zinc suspension of amylin that is crystalline, where the concentrations of amylin, zinc and protamine may be so arranged that the onset and duration of action are intermediate between those of the soluble and protamine forms of amylin; (6) the material of (5) above formulated in a suitable aqueous buffer useful for parenteral administration; (7) a preparation of crystalline zinc-amylin resuspended in a solution of sodium chloride/sodium acetate, pH 7.2–7.5, and suitable for parenteral administration; (8) amorphous insulin precipitated at high pH and suitable for parenteral administration; and, (9) a mixture of crystalline and amorphous amylin suitable for parenteral administration. Each such preparation will be suitable for parenteral administration by the subcutaneous route.

The stability of amylin preparations may be increased at neutral pH. Neutral preparations of amylin may be mixed with other neutral preparations of amylin, or with appropriate preparations of insulin, resulting in increased clinical utility. See Larner, supra.

To purify amylin from various different sources to a level useful in human therapeutics, various methods have been used. It has been demonstrated that amylin can be isolated from the human pancreas in a highly pure state by a combination of concentration using a centrifuge, gel filtration chromatography, and reverse phase chromatography, specifically HPLC. In, for example, larger scale purification of amylin, forms of chromatography other than HPLC, such as fast protein liquid chromatography (FPLC), may be useful and appropriate. Other forms of chromatography may be useful, such as ion exchange, molecular sieve, or hydrophobic interaction chromatography.

Therapy of Type 1 diabetes mellitus with transplants of islet cell tissue or whole pancreatic tissues, or with islet cell implants, may well become important treatments. Because some of the therapeutic effects of such therapy will accrue from replacement of the ability to manufacture and secrete amylin, monitoring of amylin levels will be necessary to follow the course of such therapy. Similarly, it may be necessary to monitor amylin levels in blood, serum or plasma, to assess the treatment of hypoglycemia, Type 1 diabetes mellitus, and various amylin-deficient states.

EXAMPLE

This experiment was performed to demonstrate 3 above, that amylin reduces the rate of glycogen synthesis in both basal and insulin-stimulated modes.

After having been starved overnight, rats were killed and their soleus muscles extracted and incubated in buffer at physiological pH. $^{14}$C-labelled glucose and cold (unlabelled) glucose were added and the rate of incorporation of glucose into glycogen was measured by extraction of glycogen and counting at intervals of up to six hours. The experiments were done in the presence, 1, 10, 100 and 1000 microunits of insulin per ml. Half the experiments were performed in the presence of 120 nanomoles per liter of amylin.

The results are set out in the accompany FIG. 1, which is a graph of rate of glycogen synthesis against insulin concentration. The open circles represent the results of experiments performed in the absence of amylin; the filled circles represent results of experiments performed in the presence of 15 micromoles per liter of amylin. Each spot at 1 and 100 microunits per ml insulin is the mean of 11 replicate experiments; each spot at 10 and 1000 microunits per ml insulin is the mean of 5 replicates.

At all physiological concentrations of insulin (from 1 to 100 microunits per ml), glycogen synthesis is slowed down in the presence of amylin. The differences are statistically significant (p is less than 0.05 at 1 and 100 microunits per ml by the Mann Whitney U test.

It will observed that the inhibition of glycogen synthesis by amylin persists at low, and presumably even at zero insulin concentrations. It appears that amylin has its own action which is contrary to that of insulin by probably not mediated by direct antagonism of insulin action. In support of this, it has been observed that amylin is not capable of significantly displacing insulin from its receptor on red blood cells.

I claim:

1. A method of preparing a product for treatment of a patient suffering from diabetes mellitus which comprises bringing a predetermined amount of an amylin agonist into the form of a composition suitable for parenteral administration to said diabetic patient.

2. The method of claim 1 wherein said amylin agonist is amylin.

3. The method of claim 1 wherein said amylin agonist is a conservative variant of amylin.

4. The method of claim 2 wherein said amylin is human amylin.

5. The method of claim 1 wherein said amylin agonist is CGRP.

6. The method of claim 1 wherein said amylin agonist is a conservative variant of CGRP.

7. The method of claim 5 wherein said CGRP is human CGRP.

8. The method of claim 1 wherein said parenteral administration is subcutaneous.

9. A method of preparing a composition for treatment of a patient suffering from diabetes mellitus which comprises bringing a predetermined amount of an insulin and a predetermined amount of an amylin agonist into the form of a composition suitable for parenteral administration to said diabetic patient.

10. The method of claim 9 wherein said amylin agonist is amylin.

11. The method of claim 9 wherein said amylin agonist is a conservative variant of amylin.

12. The method of claim 10 wherein said amylin is human amylin.

13. The method of claim 9 wherein said amylin agonist is CGRP.

14. The method of claim 9 wherein said amylin agonist is a conservative variant of CGRP.

15. The method of claim 13 wherein said CGRP is human CGRP.

16. The method of claim 9 wherein said insulin and said amylin agonist are in a ratio of from 100:1 to 0.1:1.

17. The method of claim 9 wherein said parenteral administration is subcutaneous.

* * * * *